United States Patent [19]

Uggeri et al.

[11] Patent Number: 5,539,105
[45] Date of Patent: Jul. 23, 1996

[54] INTERMEDIATES FOR CHELATING AGENTS WITH PREFIXED SYMMETRY AND PROCESS FOR THEIR PREPARATION

[75] Inventors: Fulvio Uggeri; Pier L. Anelli; Marcella Murru; Mario Virtuani, all of Milan, Italy

[73] Assignee: DIBRA S.p.A., Milan, Italy

[21] Appl. No.: 415,529

[22] Filed: Apr. 3, 1995

Related U.S. Application Data

[63] Continuation-in-part of Ser. No. 30,007, filed as PCT/EP91/01546 Aug. 14, 1991, published as WO92/04336 Mar.. 19, 1992, Pat. No. 5,424,423.

[30] Foreign Application Priority Data

Aug. 29, 1990 [IT] Italy ........................................ 21318/90

[51] Int. Cl.[6] ................................................ C07D 257/00
[52] U.S. Cl. ........................... 540/474; 540/472; 540/473; 540/476
[58] Field of Search ..................................... 540/474, 472, 540/473, 476

[56] References Cited

U.S. PATENT DOCUMENTS

| | | | |
|---|---|---|---|
| 4,085,106 | 4/1978 | Atkins | 260/256.4 |
| 5,424,423 | 6/1995 | Uggeri et al. | 540/474 |

*Primary Examiner*—Mukund J. Shah
*Assistant Examiner*—Pavanaram K. Sripada
*Attorney, Agent, or Firm*—Bucknam and Archer

[57] ABSTRACT

The preparation of compounds of formula (I), wherein R and $R^1$ have the meanings specified in claim 1, is disclosed compounds (I) are useful intermediates for the preparation of chelating agents.

2 Claims, 6 Drawing Sheets

FIG. 1A

PhFTAZA in COC13
2D INEPT long-range exa
nat.irr. st tne Nrl protan
U-500. Darnatant. p.s.
exp6 pules sequence: Inspt1r 2D

| SAMPLE | | DEC. E VT | |
|---|---|---|---|
| date | Jel 4 80 | dn | H1 |
| solvent | 00C13 | dat | -1260.0 |
| fils | sxp | dn | nny |
| ACQUISITION | | dmm | ccs |
| sfrq | 125.697 | dnf | 11200 |
| tn | C13 | spnr | 46 |
| st | 0.213 | tnmp | 40.0 |
| np | 512 | PROCESSING | |
| pn | 1200.0 | sb | 0.158 |
| fb | 700 | sbs | -0.099 |
| bs | 64 | wtfile | |
| os | 4 | proc | ft |
| tpnr | 57 | 1n | 512 |
| pw | 5.8 | nath | f |
| ø1 | 2.000 | | |
| tpf | -5838.8 | werr | |
| st | 5 | nexp | |
| ct | 5 | wbe | |
| sleck | n | unt | |
| pain | 35 | 2D PROCESSING | |
| saftdpnr | 17 | sbi | 0.637 |
| jnxh | 5.0 | sbsi | nat used |
| chn | 1.0 | wtfilsi | |
| delta 2 | 0 | proci | ft |
| width | 25.0 | fni | 126 |
| dofsel | 1511.5 | DISPLAY | |
| ds | 0.00025 | sp | 5435.4 |
| FLARS | | np | 1200.0 |
| il | n | vs | 244 |
| in | n | sc | 140 |
| dp | y | nc | 120 |
| bs | m | hxmm | 10.00 |
| 2D ACQUISITION | | is | 500.00 |
| swi | 20.0 | rfl | 150.6 |
| ni | 24 | rfp | 5586.0 |
| 2D DISPLAY | | th | 3 |
| spi | -9.6 | ins | 1.000 |
| wpi | 20.0 | si | cdc av |
| sc2 | 0 | | |
| wc2 | 170 | | |
| rfli | 9.8 | | |
| rfpi | 0 | | |

PhFTAZA in CDCl3
INEPT long-range experiment
nat.irr. st NN and CH2-Ph     —CHO
methylene region
U-500. Darnatant. p.s.
exp4 pules sequence: inept1r

| SAMPLE | | DEC. E VT | | ACQUISITION | ARRAYS | |
|---|---|---|---|---|---|---|
| date | Jul 4 90 | dn | Hi | array | (chn.dota | |
| solvent | CDCl3 | daf | -1260.0 | | e1) | |
| fi}s | 5x5 | dn | nny | arraydim | 2 | |
| ACQISITION | | dm | ccs | | | |
| sfrq | 125.697 | dnf | 9900 | 1 | chn | |
| tn | C13 | spnr | 45 | 1 | 1 | |
| st | 0.853 | tamp | 40.0 | 2 | 2 | |
| np | 2046 | PROCESSING | | | | |
| sw | 1200.0 | sh | 0.181 | 1 | dafsel | |
| fb | 700 | sbs | not used | 1 | 1511.6 | |
| ba | 32 | wlfile | 2 | | -792.8 | |
| sd | 8 | proc | ft | | | |
| tpwr | 57 | fn | not used | | | |
| pw | 6.8 | math | f | | | |
| di | 3.000 | | | | | |
| taf | -5838.8 | werr | | | | |
| nt | 64 | wexp | | | | |
| ct | 54 | wbs | | | | |
| aleck | n | wnt | | | | |
| pein | 20 | DISPLAY | | | | |
| softdpnr | 17 | ap | 5426.2 | | | |
| jnxh | 7.0 | wp | 1200.0 | | | |
| chn | arrayes | vs | 8362 | | | |
| delti | 0 | sc | 0 | | | |
| delta | 0 | wc | 250 | | | |
| width | 15.0 | hxmm | 4.80 | | | |
| dofsel | arrayed | is | 500.00 | | | |
| as | 0.00025 | ril | 4252.4 | | | |
| FLARS | | rip | 9576.7 | | | |
| il | n | th | 22 | | | |
| in | n | ine | 1.000 | | | |
| dp | y | si  cdc  av | | | | |
| ha | nn | | | | | |

FIG. 2B

```
PhTAZA in CDCl5 F
PR phase sens. IDADEDLIATE
J-E50. Larostadt. p.s.
exp4 pulse sequence: cccc
        SAMPLE           DEC. EVT        ACQUISITION   ARRAYS
date    Jul 1 90      dn          H1     array         phase
solvent    CDCl3      dof    -1260.0     wrraydim      64
file       exp        dm         yyy
     ACQUISITION      dmm          s  1                phase
sfrq     125.697      dof       9900  1                  1
tn           C13      dpwr        45  2                  2
at         0.427      tamp        40.0
np          1024         PROCESSING
sw        1200.0     ab         -0.332
fb           700     sbs        -0.236
ss             8     wtfile
tpnr          57     proc          ft
pw           8.8     fn          1024
d1         3.500     math           1
jcc         38.0
tof      -5838.0     werr
nt           192     nexp
ct           192     wbs
alach          0     wnt
gein          35       2D PROCESSING
     FLAGS           abi        -0.013
il             n     absi       -0.013
in             n     wtfilsi
dp             y     proci         ft
hs            nn     fni          256
    2D ACQUISITION          DISPLAY
sw1       2400.0     sp        5426.2
ni            32     np        1200.0
phase    arrayed     vs          1050
     2D DISPLAY      sc            10
sp1      10852.5     wc           240
wp1       1945.5     hxmm        5.00
sc2            0     js        500.00
wc2          150     rfl       4252.4
rf11      8594.9     rfp       9676.7
rfp1     18357.3     th             3
                     jns        1.000
                     si     cdc  p1
```

FIG. 3B

INTERMEDIATES FOR CHELATING AGENTS WITH PREFIXED SYMMETRY AND PROCESS FOR THEIR PREPARATION

This application is a continuation-in-part of U.S. Ser. No. 030,007, filed as PCT/EP91/01546 Aug. 14, 1991 published as WO92/04336 Mar. 19, 1992 now U.S. Pat. No. 5,424,423.

FIELD OF THE INVENTION

The present invention relates to 1,7-disubstituted 1,4,7,10-tetraazacyclododecanes (TAZA) which are useful intermediates for chelating agents and to a process for the preparation thereof.

BACKGROUND OF THE INVENTION

The chemistry of polyazamacrocycles with coordinating side arms, which increase the ligating ability of the macrocycles, has developed quickly over the last decade (P.V. Bernhardt and G. A. Lawrance, Coord. Chem. Rev., 1990, 104,297). Derivatives of 1,4,7,10-tetraazacyclododecane (TAZA) which contain additional donor groups, have been widely investigated due to the applications found for some of their metal complexes. Relevant examples are given by the use of the Gd complex of 1,4,7,10-tetraazacyclododecane-tetraacetic acid (DOTA) as a contrast agent for in vivo magnetic resonance imaging (M. Magerstaedt, O. A. Gansow, M. W. Brecbbiel, D. Colcher, L. Baltzer, R. H. Knop, M. E. Girton and M. Naegele, Magn. Reson. Med., 1986, 3,808) and of $^{90}Y$ complexed DOTA derivatives attached to monoclonal antibodies in radioimmunotherapy (D. Parker, Chem. Soc. Rev., 1990, 19, 271; S. V. Deshpande, S. J. De Nardo, D. L. Kukis, M. K. Moi, M. J. McCall, G. L. De Nardo and C. F. Meares, J. Nucl. Med., 1990, 31,473). Well known are derivatives of TAZA bearing four identical residues on the nitrogen atoms. On the contrary, TAZA derivatives containing different coordinating side arms on the nitrogen atoms have received little attention, likely due to the difficulties involved in their synthesis. In this context, 1,7-disubstituted-1,4,7,10-tetraazacyclododecanes can be very useful in order to obtain chelating agents with prefixed symmetry. These compounds can, in principle, be synthesized (T. A. Kaden, Top. Curr. Chem., 1984, 121, 154) by classical condensation according to Richman and Atkins (J. E. Richman and T. J. Arkins, J. Am. Chem. Soc., 1974, 96, 2268; T. J. Atkins, J. E. Richman and W. F. Oettle, Org. Synth., 58, 86). However, the nature of the residues, which can be introduced into positions 1 and 7 by this synthetic approach, is severely limited by the harsh conditions required, in particular during the deprotecting steps.

SUMMARY OF THE INVENTION

A preferred embodiment of this invention relates to these compounds useful for the selective preparation of chelating agents with prefixed symmetry, said compounds consisting of 1,7-disubstituted derivatives of 1,4,7,10-tetraazacyclodecane of general formula (I)

wherein
R is a formyl group
$R_1$ is: a) a straight or branched alkyl group $C_1$–$C_{20}$, which is unsubstituted or substituted by a group able to bind to proteins, such as OH, $NH_2$, COOH, CHO, SH or by their precursors such as $NO_2$, NO, CN, COOR, b) a phenylalkyl group $C_7$–$C_{19}$ which is unsubstituted or substituted on the phenyl radical by one or more $C_1$–$C_4$ alkyl, $C_1$–$C_4$ alkoxy or halogen groups or by groups able to bind to proteins such as for example OH, $NH_2$, COOH, CHO, SH or by their precursors such as $NO_2$, NO, CN, COOR, c) a group alkoxy($C_1$$C_4$)carbonylmethyl or 2-[alkoxy($C_1$–$C_4$)carbonyl]ethyl, d) a group of formula:

$-(CH_2)_n-R_2$ wherein n=1–4 and $R_2$ is a free formyl group or an acetal group.

The compounds of formula I are meant for the preparation of chelants with prefixed symmetry derived from 1,4,7,10-tetraazacyclododecane, by substituting the hydrogen atoms in 4 and 10 positions with specific functional groups, if necessary after converting the formyl group in 1- and/or the substituents in 7-position of the macrocycle into other suitable groups.

Non-limiting examples of compounds of formula (I) are the ones wherein $R_1$ is alkyl $C_6$–$C_{18}$, benzyl, triphenylmethyl, t-butoxycarbonyl methyl, or a group of formula $-(CH_2)_n-R_2$ wherein n=1 or 2 and $R_2$ is a group $-CH(OCH_3)_2$, $-CH(OC_2H_5)_2$ or 1,3-dioxol-2-yl.

Another preferred embodiment of the invention relates to a process for the preparation of compounds of formula (I).

Reaction of the TAZA compounds with dimethylformamide diethylacetal afforded the expected monoalkyl orthoamide protected macrocycles hereinbelow (structure 1). These compounds, after treatment under the hydrolytic conditions with $H_2O$-EtOH at room temperature were expected to yield a mixture of two regioisomers, namely the 1,4 and the 1,7 disubstituted derivatives, that is compounds 2 and 3. Mechanisms possibly involved in the hydrolytic ring opening of the tricyclic Structure 1 are reported in the hereinbelow Scheme. No theoretical reasons existed against either of the two foreseeable hydrolytic routes. As a matter of fact, neither steric hindrance considerations nor possible differences in basicity of the four nitrogen atoms could be reasonably taken into account to infer that a preferential route was to be expected. Therefore, a mixture of 1,4 vs 1,7 regioisomer respectively should have been obtained.

Therefore, it was surprising that, for example, the hydrolysis of the orthoamide protected N-benzyl-1,4,7,10-tetraazacyclododecane afforded one largely major product together with small amounts of impurities accounting for a few percent of the crude mixture.

route A route B

Assignment of the structure to this compound by NMR was not easy. Indeed some preliminary considerations about NMR spectra of TAZA derivatives are necessary to clarify this issue.

The determination of the structure of the product, that is the 1,7-disubstituted 1,4,7,10-tetraazacyclododecane (compound 2) instead of the 1,4-isomer compound 3) was carried out as described hereinbelow.

Figure 1A:
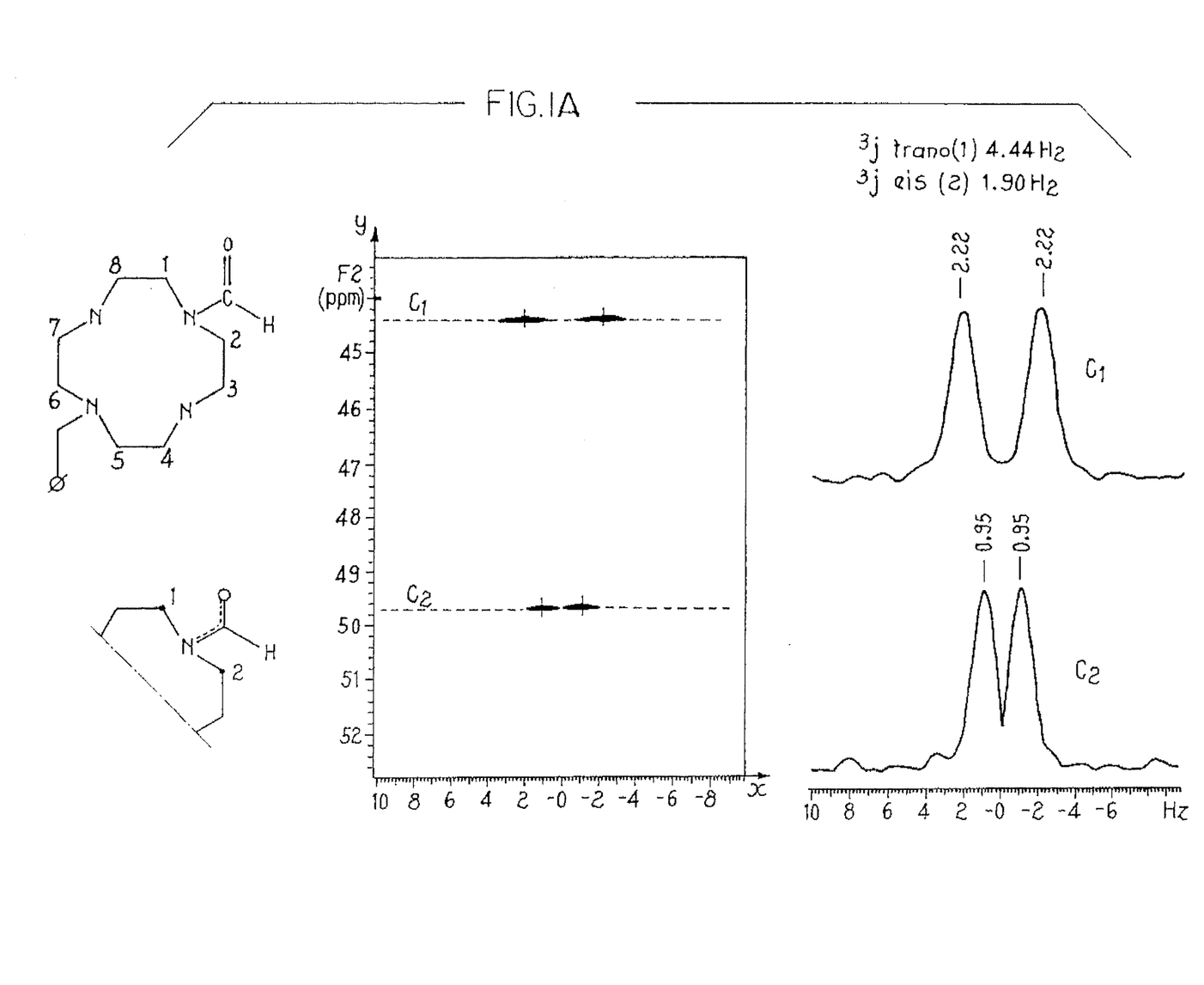
Figure 1B:
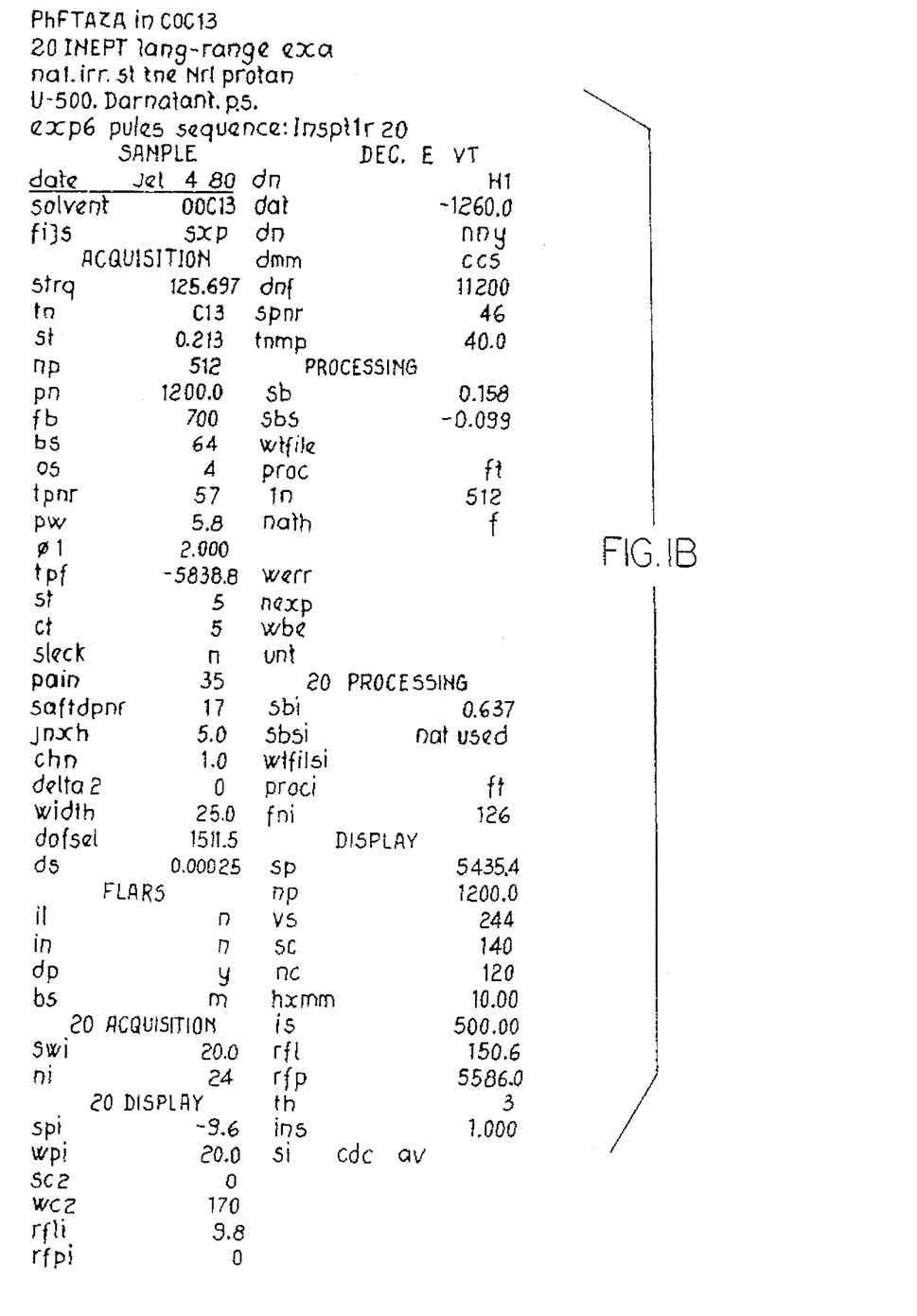
Figure 2A:
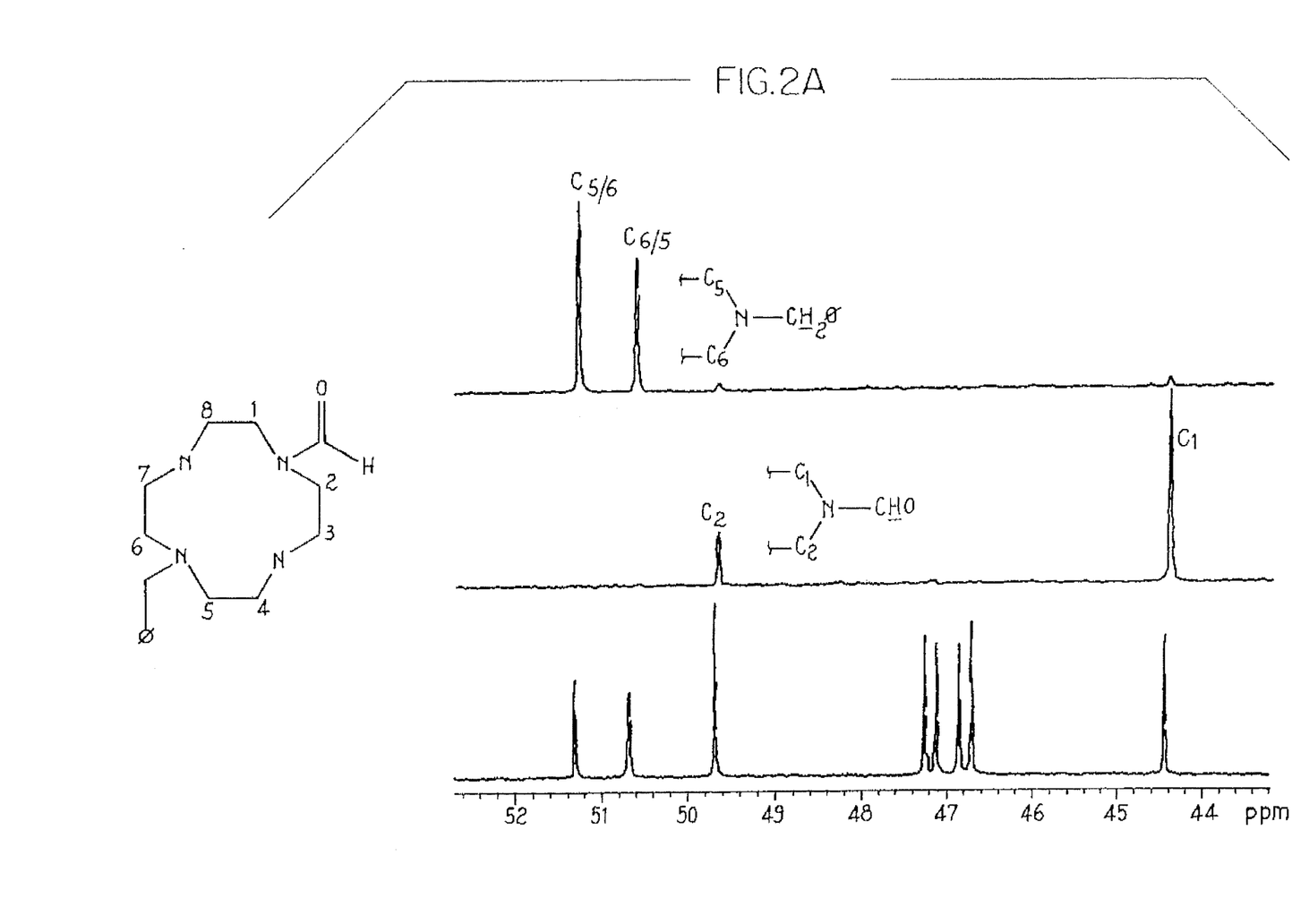
Figure 2B:
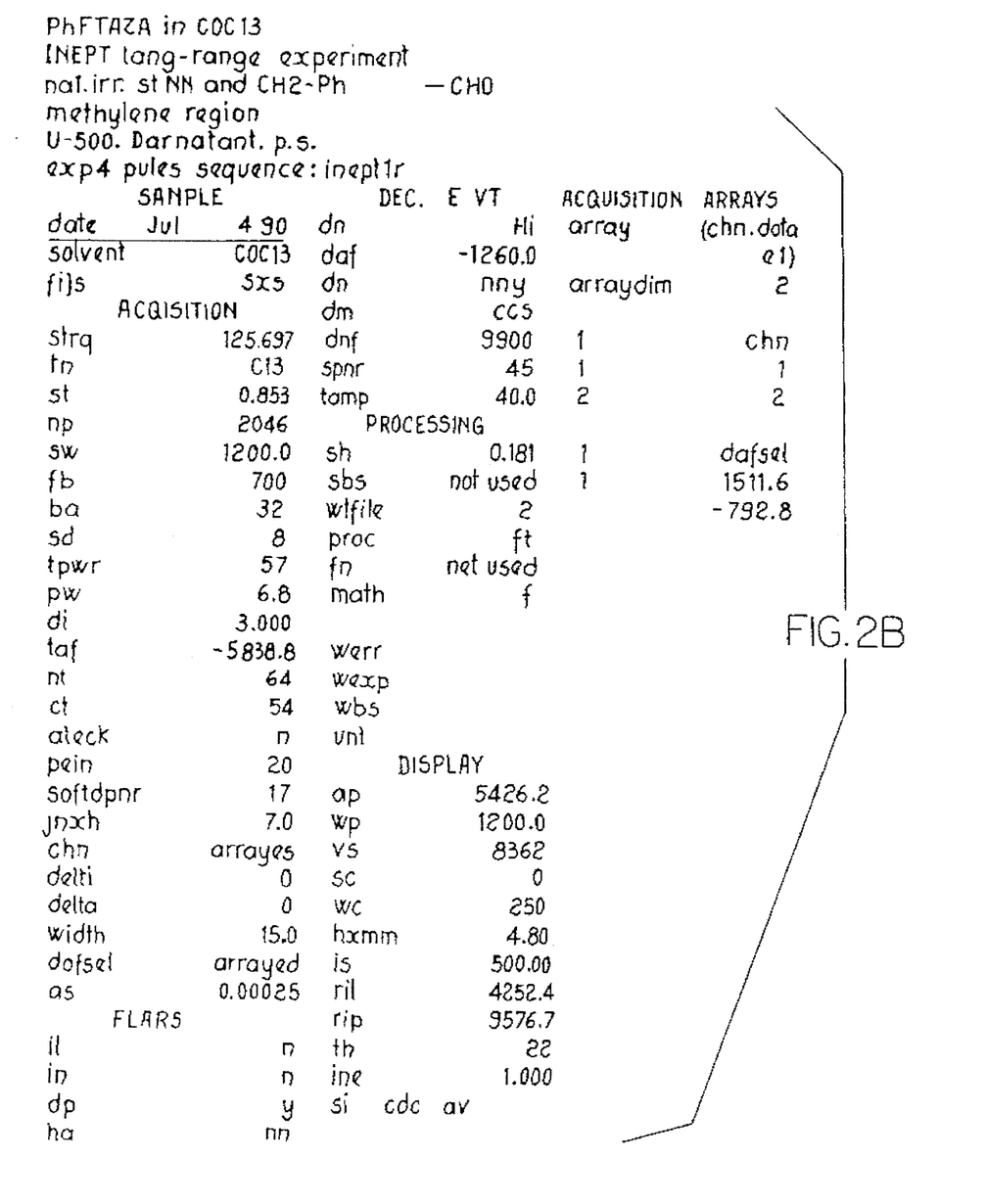
Figure 3A:
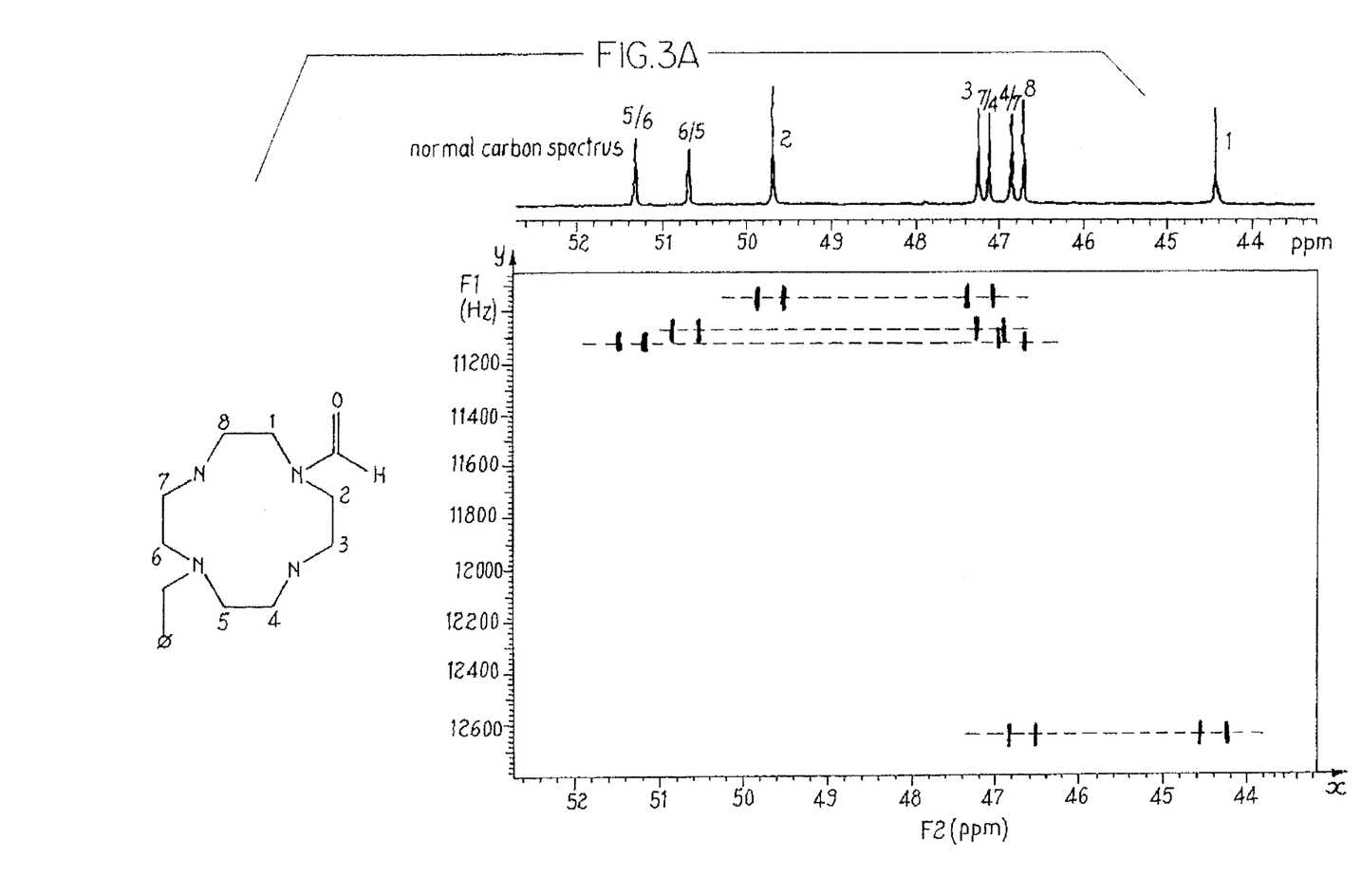
Figure 3B:
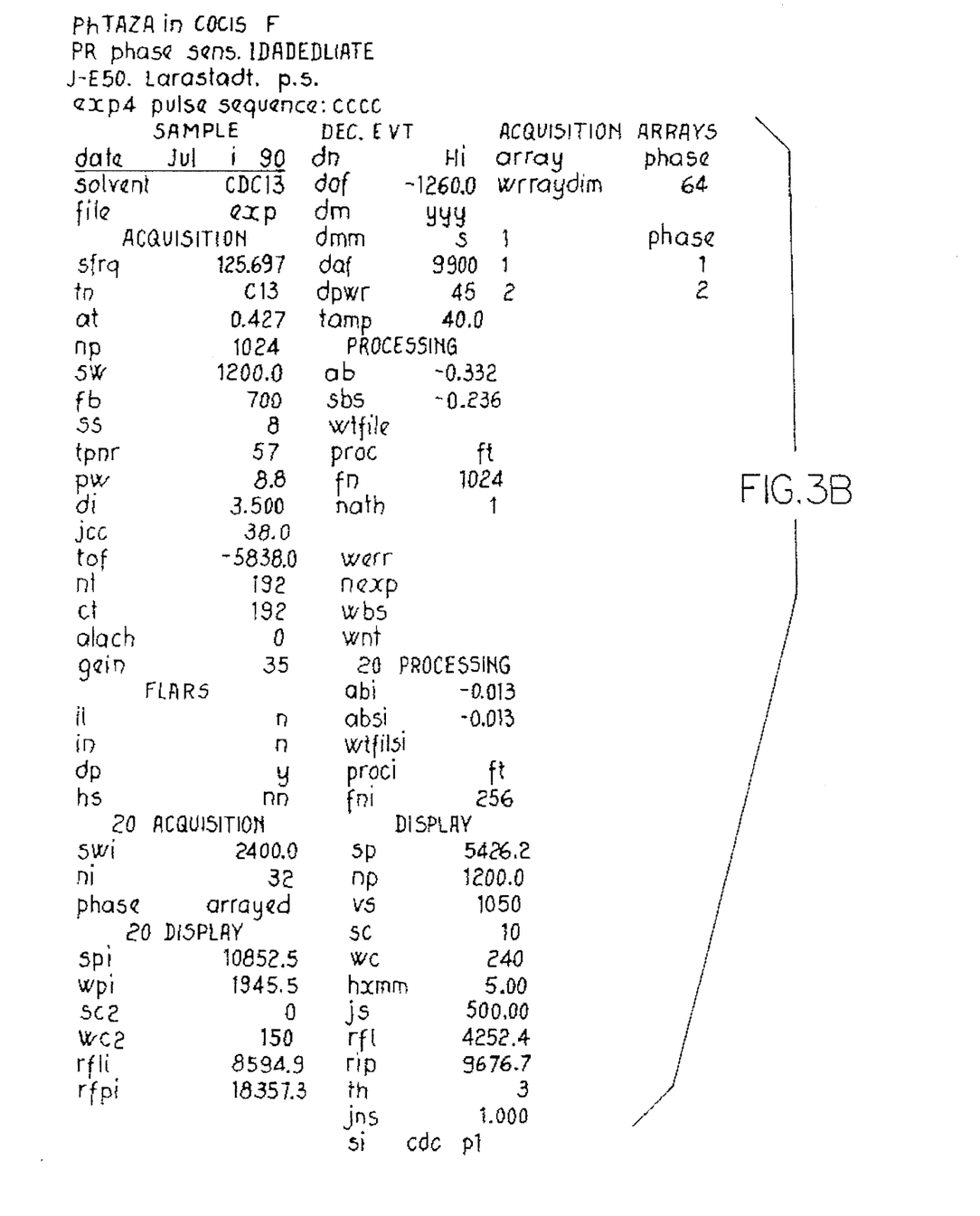

N-Monoalkylated TAZA derivatives show $^{13}$C-NMR with only four signals for the eight ring carbon atoms due to fast conformational interchange. The same is true also for the polyalkylated TAZA derivatives which show fewer NMR signals than expected. On the contrary, once a formyl group is introduced on one of the ring nitrogen atoms, the conformational interchange is slowed down to such an extent that all the methylenes of the TAZA ring become anisotropic and for example in N-formyl-TAZA eight signals are seen for the eight ring carbons. Therefore the presence of a N-formyl group made necessary to perform non-conventional experiments to allow assignment of the structure in the present case to distinguish between 1,4 and 1,7-derivatives. For this purpose INEPT (Insensitive Nuclei Enhanced by Polarization Transfer) long range and INADEQUATE (Incredible Natural Abundance Double Quantum Transfer Experiment) experiments were performed (Atta-ur-Rahman, "One and two dimensional NMR spectroscopy", Chapters 2 and 3, Elsevier, 1989). The results of these experiments are shown in FIGS. 1 to 3.

BRIEF DESCRIPTION OF THE DRAWINGS

FIG. 1 shows the result of the INEPT experiment which has made possible the assignment of the signals due to the two C atoms of the macrocycle ring (C1 and C2) which are linked to the nitrogen atom carrying the formyl group;

FIG. 2 shows the result of the INEPT experiment which has made possible the assignment of the signals due to the two C atoms of the macrocycle ring (C5 and C6) which are linked to the nitrogen atom carrying the benzyl group.

FIG. 3 shows the result of the INADEQUATE experiment which has made possible to understand the carbon-carbon connection along the macrocycle ring.

FIGS. 1, 2 and 3 are copies of photos of the original spectra recorded at Varian, Darmstadt, Germany on a Varian 500 MHZ instrument on July 1–4, 1990.

The INEPT experiment consists of a selective excitation of the protons of interest and, together with the use of a correct value of the coupling constants J, makes it possible to assign the signals due to carbon atoms three bonds away from the excited proton. Specifically in this case, with a TAZA derivative bearing both a formyl and a benzyl group, selective excitation of the formyl proton, allowed to assign the two carbon atoms C1 and C2 (FIG. 1) which are linked to the nitrogen atom carrying the formyl residue. Because of the fact that there is no free rotation around the $N-C_{formyl}$ bond C1 and C2 can be distinguished due to the different values of the two J constants ($J_{trans}$=4.44 Hz for C1 and $J_{cis}$=1.90 Hz for C2) and consequently can be definitively assigned (C1 at 44.4 ppm and C2 at 49.7 ppm respectively).

Similarly, selective excitation of the two benzyl atoms allowed to assign the two carbon atoms C5 and C6 (FIG. 2), which are linked to the nitrogen atom carrying the benzyl group. In this case, however, C5 and C6 are not distinguishable between them, due to the free rotation around the $N-C_{benzyl}$ bond. Therefore, they were indifferently assigned to 50.7 ppm and ~51.3 ppm).

What was really remarkable in order to definitively assign the structure of the molecule was the INADEQUATE experiment. This is a fully proton decoupled experiment which permits the detection of $13_C-13_C$ directly bonded atoms and in our case allowed to understand the carbon-carbon connection along the macrocycle ring. In this experiment, the signals at the same frequency $F_1$ reported on the y axis, as shown in FIG. 3) indicate that the corresponding carbon atoms are directly linked between them. FIG. 3 clearly shows that neither C1 or C2 is directly bound to either C5 or C6 because their signals are recorded at different frequencies. To be more precise C1, which gives a signal at 44.4 ppm, results to be bonded to the carbon atom at 46.7 ppm, while C2 (at 49.7 ppm) is connected to the carbon atom at ~47.3 ppm. On the other hand, one of the two carbons C5 and C6, i.e. the one at 50.7 ppm, results to be linked to the carbon atom at ~47.1 ppm, while the other one (at ~51.3 ppm) is bonded to the carbon atom at ~46.9 ppm. This situation is perfectly consistent with the macrocycle 1,7-disusbstituted structure. On the contrary, in case of 1,4-disubstitution, a completely different spectrum of frequencies should have been recorded.

The reaction sequence, that is triprotection and hydrolytic ring opening, was repeated on a number of N-monoalkyl derivatives of TAZA. In all cases, the formation of only one regioisomer was obtained and the structure was confirmed to be that of the 1,7-disubstituted derivative. The structure of the 1,7-regioisomers has been further confirmed by X-ray crystal structure analysis performed on single crystals of the hydrolysis product of the orthoamide TAZA derivative bearing a triphenylmethyl residue. Therefore the reaction scheme hereinbelow is proper.

According to this scheme, the mono-substituted compounds of formula (II) (where $R_1$ has the meanings given above) are converted, by reaction with dialkylacetals of N,N-dialkylformamide of formula (III) (where $R_3$ and $R_4$, equal or different between them, are alkyl groups $C_1$–$C_4$, preferably ethyl or methyl), into the corresponding derivatives of formula (IV) and these ones are then submitted to hydrolysis.

The preparation of $R_1$-substituted 1,4,7,10-tetraazacyclododecanes of formula (II) occurs by reacting a compound of formula $R_1$-X (where X is the leaving group, preferably halogen such as chlorine or bromine) with an excess of 1,4,7,10-tetraazacyclododecane, in an inert solvent, for example acetonitrile. The molar ratio between $R_1$-X and tetraazacyclododecane ranges from 1:5 to 1:15, and preferably is 1:10. The condensation is preferably carried out at the refluxing temperature of the solvent. When the reaction ends, the cooling of the mixture causes the precipitation of the tetraazacyclododecane in excess, which is recovered. After elimination of the solvent, the desired compound is purified by crystallization or chromatography.

The conversion of the $R_1$-substituted 1,4,7,10-tetraazacyclododecanes of formula (II) into the corresponding derivatives of formula (IV) can be made according to the procedure disclosed in the European patent EP 292689 (M. F. Tweedle et al., 1988) in which 1,4,7,10-tetraazacyclododecane is reacted with a N,N-dialkylformamide-dialkylacetal (III) (preferably the dimethyl- or diethylacetal of dimethylformamide) in a solvent like aromatic, aliphatic or cycloaliphatic hydrocarbons or halohydrocarbons, dialkylethers, alkylnitriles, at a temperature ranging from 60° C. to 180° C., preferably at the boiling point of the solvent, distilling the azeotropic mixture alcohol-solvent and the dialkylamine which are formed. It is better to use an excess of (III), preferably 2–4 mol/mol of (II). After evaporation of the solvent under reduced pressure, the derivatives (IV) are directly isolated, generally as very pure oils. Such derivatives are new (excluding the 1-ethylderivative described in U.S. Pat. No. 4085106) and they too are part of the present invention.

Alternatively, the tricyclic compounds (IV) are obtained by alkylating the unsubstituted octahydrodtetraazacyclooctapentalen (V) with the above mentioned $R_1$-X compounds:

Compound (V) is formed by 1,4,7,10-tetraazacyclododecane and dimethylformamide-dialkylacetal, as disclosed in U.S. Pat. No. 4,085,106.

The hydrolysis of derivatives of formula (IV) is obtained by heating the mentioned compounds in a hydroalcoholic solution (preferably water/methanol or water/ethanol). The ratio water/alcohol ranges from 1:3 and 3:1 (v/v), and preferably is 1:1. The reaction temperature is not critical, it can range from room to reflux temperature. When the hydrolysis is finished, the solvent is removed under reduced pressure and the compounds of formula (I) are isolated from the residue by means of crystallization or chromatography. The following examples relate to the process according to the present invention.

EXAMPLE 1

1-Benzyl-1,4,7,10-tetraazacyclododecane

A solution of benzyl bromide (4.96 g; 0.029 mol) in acetonitrile (50 ml) is added in 1 h to a solution of 1,4,7,10-tetraazacyclododecane (50 g, 0.29 mol) in acetonitrile (450 ml) at refluxing temperature of the solvent and under inert atmosphere.

After 30 minutes from the end of the addition, the reaction mixture is cooled at 5 C and part of the 1,4,7,10-tetraazacyclododecane in excess precipitate. After filtration, the reaction mixture is evaporated under reduced pressure. The residue, dissolved in 5% aqueous solution of sodium carbonate (200 ml), is extracted with toluene (3×200 ml). The organic phase is washed with water (100 ml), anhydrified ($Na_2SO_4$) and evaporated to dryness. After crystallization by petrol ether (m.p. 40–60 C), the desired product is obtained (6.8 g) as a white solid. Yield 89%.

m.p. : 85 C.

Titre : 98% (G.C.)

$^1$H-NMR ($CDCl_3$):δ2.4 (m, 8H); 2.5 (m, 4H); 2.6 (bt, 4H); 3.4 (bs, 2H); 7.2 (bm, 5H).

$^1$H-NMR ($CDCl_3$):δ44.90; 46.13; 46.98; 51.03; 59.04; 126.84; 128.11; 128.80; 138.74.

M.S. (EI): 262 ($M^{+}$)

| Elemental Analysis for $C_{15}H_{26}N_4$ (%): | | | |
|---|---|---|---|
| | C | H | N |
| Calculated | 68.66 | 9.99 | 21.35 |
| Found | 68.49 | 10.04 | 21.15 |

Using the same procedure the following compounds were prepared:

a) 1-hexadecyl-1,4,7,10-tetraazacyclododecane

Colorless oil. Yield 82%.

Titre : 99% (G.C.)

$^1$H-NMR ($CDCl_3$): δ1 00 (bt 3H); 1.25 (bs 28H); 2.4–3.0 (m, 18H).

$^{13}$C-NMR ($CDCl_3$): δ13.96; 22.53; 27.4–29.6; 31.79; 45.16; 46.08; 47.03; 52.30; 54.42.

M.S. (EI) :396 ($M^{+}$)

| Elemental Analysis for $C_{24}H_{52}N_4$ (%): | | | |
|---|---|---|---|
| | C | H | N |
| Calculated | 72.66 | 13.21 | 14.12 |
| Found | 72.44 | 13.31 | 13.82 | b) 1-dodecyl,1,4,7,10,tetraazacyclododecane

Colorless oil. Yield 86%

Titre : 96% (G.C.)

$^1$H-NMR ($CDCl_3$):δ1.0 (t, 3H);1.45–1.55 (bs, 20H); 2.5–3.2 (m, 18H)

$^{13}$C-NMR ($CDCL_3$): δ14.00; 22.55; 26.60–29.60; 31.80; 44.74; 45.63; 46.60; 51.11; 54.29

M.S. (EI): 340 ($M^{+}$)

| Elemental Analysis for $C_{20}H_{44}N_4$ (%): | | | |
|---|---|---|---|
| | C | H | N |
| Calculated | 70.50 | 13.04 | 16.45 |
| Found | 70.01 | 12.96 | 16.28 |

| Elemental Analysis for $C_{16}H_{36}N_4$ (%): | | | |
|---|---|---|---|
| | C | H | N |
| Calculated | 67.52 | 12.77 | 19.69 |
| Found | 66.84 | 12.64 | 19.49 | d) 1-[t-butoxycarbonyl)methyl]-1,4,7,10tetraazacyclododecane

Colorless oil. Yield 58%

Titre : 97% (G.C.)

$^1$H-NMR ($CDCl_3$): δ 1.75 (s, 9H); 2.85–3.15 (bm, 16H); 3.57 (bs, 2H)

$^{13}$C-NMR ($CDCl_3$): δ27.92; 44.99; 45.80; 46.71; 51.54; 56.78; 90.65; 170.08

M.S. (EI): 286 ($M^{+}$)

| Elemental Analysis for $C_{14}H_{30}N_4O_2$ (%): | | | |
|---|---|---|---|
| | C | H | N |
| Calculated | 58.71 | 10.56 | 19.56 |
| Found | 58.60 | 10.63 | 19.54 |

EXAMPLE 2

1-[2-(1,3-dioxol-2-yl)ethyl]-1,4,7,10-tetraazacyclododecane

A solution of 2-(2-bromoethyl)-1,3-dioxolane (16.08 g; 0.087 mol) acetonitrile (1) is added in 2 h to a solution of 1,4,7,10-tetraazacyclododecane (150 g; 0.87 mol) in acetonitrile (2 l) at refluxing temperature and under inert atmosphere. After 30 minutes from the end of the addition, the reaction mixture is cooled at 5° C. and the precipitate obtained is removed by filtration. After evaporation of the solution under reduced pressure, the residue is solubilized in boiling ethyl acetate. When the solution is cooled at 5° C., another part of 1,4,7,10-tetraazacyclcdodecane precipitates. After filtration, the solvent is evaporated under reduced pressure and the residue is purified by column chromatography [Silica gel; isopropanol/chloroform/triethylamine=6/4/2 (v/v/v) ].

The product obtained is a colorless oil (20.8 g).

Yield 88%.

Titre : 96% (G.C.)

$^1$H-NMR ($CDCl_3$): δ1.9 (m, 2H); 2.6–2.7 (m, 14H); 2.8 (m, 4H); 3.8–4.0 (m, 4H); 4.9 (t, 1H)

$^{13}$C-NMR ($CDCl_3$): δ31.05; 44.58; 45.69; 46.53; 48.76; 50.96; 64.29; 102.93

M.S. (EI) : 272 ($M^{+}$)

Elemental Analysis for $C_{13}H_{28}N_4O_2$ (%):

|  | C | H | N |
|---|---|---|---|
| Calculated | 57.30 | 10.38 | 20.57 |
| Found | 56.93 | 10.48 | 20.77 |

By using the same procedure the following compounds were prepared:

a)   1-[(1,3-dioxol-2-yl)methyl]-1,4,7,10-tetraazacyclododecane

Colorless oil. Yield 85%

Titre : 97% (G.C.)

$^1$H-NMR (CDCl$_3$):δ2.7–3.0 (m, 18H); 4.0–4.2 (m, 4H); 5.1 (t, 1H)

$^{13}$C-NMR (CDCl$_3$): δ44.81; 45.94; 46.62; 51.92; 56.68; 4.45; 103.06

Elemental Analysis for $C_{12}H_{26}N_4O_2$ (%):

|  | C | H | N |
|---|---|---|---|
| Calculated | 55.76 | 10.16 | 21.68 |
| Found | 56.43 | 10.34 | 21.92 | b) 1-[2,2-(dimethoxy)ethyl]-1,4,7,10-tetraazacyclododecane

Colorless oil. Yield 90%

Titre : 98% (G.C.)

$^1$H-NMR (D$_2$O) : δ2.4–2.7 (m, 18H); 3.4 (b, 6H); 4.45 (t, 1H)

$^{13}$C-NMR(D$_2$O):δ46.16; 47.48; 47.90; 54.28; 57.21; 58.26; 106.81

Elemental Analysis for $C_{12}H_{28}N_4O_2$ (%):

|  | C | H | N |
|---|---|---|---|
| Calculated | 55.33 | 10.85 | 21.51 |
| Found | 54.77 | 10.74 | 21.29 |

EXAMPLE 3

1-triphenylmethyl-1,4,7,10-tetraazacyclododecane

A solution of triphenylchloromethane (8.08 g; 0.029 mol) in acetonitrile (250 ml) is added in 2 h to a solution of 1,4,7,10-tetraazacyclododecane (50 g; 0.29 mol) in acetonitrile (500 ml) at 40 C. under inert atmosphere.

After one hour from the end of the addition, the reaction mixture is cooled at 5° C. and part of 1,4,7,10-tetraazacyclododecane in excess precipitates. After removing the solid by means of filtration, the reaction mixture is evaporated under reduced pressure and the residue is diluted with water (500 ml). The resulting suspension is filtered and the solid is washed with water ( 500 ml). After purification by chromatography [Silica gel; ethyl acetate/6N ammonia in methanol=3/1 ( v/v )] the desired product is obtained as a white glass solid (9.1 g). Yield 75% m.p. 70–71 C $^1$H-NMR (CDCl$_3$): δ2.9–3.5 (m, 16H); 7.5–8.3 (m, 15H)

$^{13}$H-NMR ( CDCl$_3$): δ43.60; 47.29; 49.47; 54.42; 79.37; 126.13; 127.55; 129.95; 143.72

Elemental Analysis for $C_{27}H_{34}N_4$ (%):

|  | C | H | N |
|---|---|---|---|
| Calculated | 78.22 | 8.27 | 13.51 |
| Found | 78.02 | 8.30 | 13.41 |

EXAMPLE 4

7-benzyl-octahydro-5H ,9bH-2a,4a, 7,9a-tetraazacycloocta[cd]pentalene

A solution of 1-benzyl-1,4,7,10-tetraazacyclododecane (4 g; 0.015 mol ) and dimethylformamide diethylacetal (6.88 g; 0.0467 mol) in benzene (40 ml) is heated at 80° C. and the azeotropic mixture ethanol-benzene is distilled away. When the conversion is ended, the solvent is evaporated under reduced pressure and the final product is obtained as a yellow oil (4.0 g). Yield 96%

Titre : 100% (G.C.)

$^1$H-NMR (CDCl$_3$): δ2.3–3.0 (m, 16H); 3.6 (s, 2H); 5.0 (s, 1H); 7.1–7.3 (m, 5H)

$^{13}$C-NMR (CDCl$_3$): δ50.93; 51.86; 52.42; 55.25; 63.28; 97.73; 126.76; 127.97; 129.09; 139.62

Elemental Analysis for $C_{16}H_{14}N_4$ (%):

|  | C | H | N |
|---|---|---|---|
| Calculated | 70.53 | 8.89 | 20.56 |
| Found | 70.14 | 8.85 | 20.18 |

By using the same procedure the following compounds were prepared:

a) 7- [t-butoxycarbonyl )methyl]-octahydro-5H, 9bH-2a, 4a,7,9a-tetraazacycloocta[cd]-pentalen Colorless oil. Yield 95%

Titre : 99% (G.C.)

$^1$H-NMR (CDCl$_3$): δ 1.75 (s, 9H); 2.8–3.35 (m, 16H); 3.65 (s, 2H); 5.2 (s, 1H)

$^{13}$C-NMR (CDCl$_3$):δ27.79; 50.51; 51.77; 52.36; 54.64; 59.13; 80.16; 99.58; 170.66

Elemental Analysis for $C_{15}H_{28}N_4O_2$ (%):

|  | C | H | N |
|---|---|---|---|
| Calculated | 60.76 | 9.53 | 18.90 |
| Found | 60.15 | 9.43 | 18.71 | b) 7-[2-(1,3-dioxol-2-yl)ethyl)]-octahydro-5H,9bH-2a, 4a, 7,9a-tetraazacycloocta[cd]pentalene.

Colorless oil. Yield 95%

Titre : 95% (G.C.)

$^1$H-NMR (CDCl$_3$):δ1.9 (m, 2); 2.7–3.4 (m, 18h); 3.8–4.0 (m, 4H); 4.9 (s, 1H) 5.2 (s, 1H)

$^{13}$C-NMR (CDCl$_3$) δ31.05; 49.84; 50.90; 51.98; 52.45; 55.23; 64.43; 98.48; 102.89

Elemental Analysis for C$_{14}$H$_{26}$N$_4$O$_2$ (%):

|  | C | H | N |
| --- | --- | --- | --- |
| Calculated | 59.53 | 9.29 | 19.84 |
| Found | 60.13 | 9.41 | 20.24 |

Elemental Analysis for C$_{14}$H$_{26}$N$_4$O$_2$ (%):

|  | C | H | N |
| --- | --- | --- | --- |
| Calculated | 59.53 | 9.29 | 19.84 |
| Found | 58.93 | 9.20 | 19.64 |

EXAMPLE 5

7-benzyl-1-formyl,1,4,7,10-tetraazacyclododecane

A solution of 7-benzyl-octahydro-5H, 9bH-2a,4a,7,9a, tetraazacycloocta[cd]-pentalen (4 g; 0.015 mol) in water/ethanol 1:1 (v/v) (50 ml) is heated under reflux for 1 h. After evaporation of the solvent under reduced pressure, the residue is crystallized from ethyl acetate and the desired product is obtained (3.3 g) as a white solid. Yield 75% m.p.: 64–65 C

Titre : 96% (G.C.)

$^1$H-NMR (CDCl$_3$): δ2.6 (m, 8H); 2.7 (t, 2H); 2.9 (t, 2H); 3.4 (t, 2H); 3.5 (t, 2H); 3.6 (s, 2H); 7.2–7.3 (m, 5H); 8.1 (s, 1)

$^{13}$C-NMR (CDCl$_3$): δ 44.40; 46.70; 46.80; 47.05; 47.30; 49.94; 50.5; 51.15; 59.39; 126.72; 128.03; 128.51; 139.51; 164.20

M.S. (EI): 290 (M$^{+}$)

Elemental Analysis for C$_{16}$H$_{26}$N$_4$O (%):

|  | C | H | N |
| --- | --- | --- | --- |
| Calculated | 66.15 | 9.04 | 19.30 |
| Found | 66.21 | 9.06 | 19.28 |

Using the same procedure the following compounds were prepared:

a) 7-[2-(1,3-dioxol-2-yl )ethyl]-1-formyl-1,4,7,10-tetraazacyclododecane

Yield : 75%

Titre : 96% (G.C.)

$^1$H-NMR (CDCl$_3$): δ2.1 (t, 2H); 2.7–3.1 (m, 14H); 3.75 (m, 4H); 4.2 (bd, 4H); 5.2 (t, 1H); 8.1 (s, 1H) $^{13}$NMR (CDCl$_3$): δ13.31; 44.37;46.70; 46.84; 46.97; 47.1; 49.55; 49.99; 50.45; 51.02; 64.53; 102.82; 164.23

Elemental Analysis for C$_{14}$H$_{28}$N$_4$O$_3$ (%):

|  | C | H | N |
| --- | --- | --- | --- |
| Calculated | 55.96 | 9.41 | 18.65 |
| Found | 56.16 | 9.52 | 18.31 | b) 7-[(t-butoxycarbonyl)methyl-1-formyl-1,4,7,10-tetraazacyclododecane

The compound is purified by means of column chromatography (Silica gel; methanol/28% aqueous ammonia—10/1 (v/v)]

Colorless oil. Yield 73%

Titre: 95% (G.C.)

$^1$H-NMR (CDCl$_3$): δ1.4 (s, 9H); 2.4–2.7 (m, 12H); 3.2 (s, 2H); 3.3–3.5 (m, 4H); 8.0 (s, 1H)

$^{13}$C-NMR (CDCl$_3$): δ27.71; 43.23; 46.37; 46.70; 46.93; 49.57; 50.51; 51.70; 55.77; 80.38; 164.38; 170.68

Elemental Analysis for C$_{15}$H$_{30}$N$_4$O$_3$ (%):

|  | C | H | N |
| --- | --- | --- | --- |
| Calculated | 57.28 | 9.63 | 17.82 |
| Found | 57.50 | 9.88 | 17.51 |

What is claimed is:

1. A process for the preparation of a compound of formula I wherein

R is a formyl group,

R$_1$ is: a) a straight or branched alkyl group C$_1$–C$_{20}$, which is unsubstituted or substituted by a group capable of binding to a protein, said group being OH, NH$_2$, COOH, CHO or SH or by a precursor thereof, said precursor being NO$_2$, NO, CN, or COOR, or b) a phenylalkyl group C$_7$–C$_{19}$ which is unsubstituted or substituted on the phenyl radical by one or more C$_1$–C$_4$ alkyl, C$_1$–C$_4$ alkoxy or halogen groups or by a group able to bind to a protein, said group being OH, NH$_2$, COOH, CHO or SH or a precursor thereof, said precursor being NO$_2$, NO, CN, or COOR, or c) a group alkoxy(C$_1$–C$_4$)carbonylmethyl or 2-[alkoxy(C$_1$–C$_4$) carbonyl]ethyl, or d) a group of formula:

—(CH$_2$)$_n$—R$_2$ wherein n=1–4 and R$_2$ is a formyl group or an acetal group which consists of reacting a 1-substituted tetraazacyclododecane of formula II with a dialkylacetal of a N,N-dialkyl formamide of formula III, whereby a tricyclic 7-substituted tetraazacyclododecane of formula IV is obtained and hydrolyzing said compound of formula IV according to the reaction scheme hereinbelow -continued whereby said compound of formula I is obtained.

2. A process for the preparation of a compound of formula (I):

wherein:

R is a formyl group, R₁ is: a) a straight or branched alkyl group $C_1$–$C_{20}$, which is unsubstituted or substituted by a group capable of binding to a protein, said group being OH, $NH_2$, COOH, CHO or SH or by a precursor thereof, said precursor being $NO_2$, NO, CN, or COOR, or b) a phenyl alkyl group $C_7$–$C_{19}$ which is unsubstituted or substituted on the phenyl radical by one or more $C_1$–$C_4$ alkyl, $C_1$–$C_4$ alkoxy or halogen groups or by a group able to bind to a protein, said group being OH, $NH_2$, COOH, CHO or SH or a precursor thereof, said precursor being $NO_2$, NO, CN, or COOR, or c) a group alkoxy ($C_1$–$C_4$)carbonylmethyl or 2-[alkoxy($C_1$–$C_4$) carbonyl]ethyl, carbonyl]ethyl, or d) a group of formula:

—$(CH_2)_n$—$R_2$ wherein n=1–4 and $R_2$ is a formyl group or an acetal group, which consists of alkylating a compound of formula V with $R_1X$, said compound of formula V being prepared from 1,4,7,10-tetraazacyclododecane by reaction with a dimethylformamide dialkylacetal, wherein $R_1$ has the same meaning as hereinabove to obtain a compound of formula IV and hydrolyzing said compound of formula IV according to the reaction scheme hereinbelow.

* * * * *